United States Patent
Valla et al.

(10) Patent No.: US 9,427,012 B2
(45) Date of Patent: Aug. 30, 2016

(54) PROCESS OF MANUFACTURING A STABLE SOFTGEL CAPSULE CONTAINING MICROENCAPSULATED PROBIOTIC BACTERIA

(75) Inventors: Claudia Valla, Piacenza (IT); Rosa Bertolami, Rome (IT); Giovanni Rosina, Trecate (IT); Karen Helson, Cumnor (GB)

(73) Assignee: R.P. Scherer Technologies, LLC, Carson City, NV (US)

( * ) Notice: Subject to any disclaimer, the term of this patent is extended or adjusted under 35 U.S.C. 154(b) by 0 days.

(21) Appl. No.: 13/204,979

(22) Filed: Aug. 8, 2011

(65) Prior Publication Data

US 2012/0039998 A1 Feb. 16, 2012

Related U.S. Application Data

(60) Provisional application No. 61/372,350, filed on Aug. 10, 2010.

(51) Int. Cl.
*A23L 1/30* (2006.01)
*A23L 1/00* (2006.01)

(52) U.S. Cl.
CPC ............ *A23L 1/3014* (2013.01); *A23L 1/0029* (2013.01); *A23L 1/3006* (2013.01)

(58) Field of Classification Search
CPC .. A23L 1/0029; A23L 1/3006; A23L 1/3014
See application file for complete search history.

(56) References Cited

U.S. PATENT DOCUMENTS

| | | |
|---|---|---|
| 6,008,027 A | 12/1999 | Langner |
| 2003/0147857 A1 | 8/2003 | Monte |
| 2004/0223956 A1 | 11/2004 | Naidu et al. |
| 2005/0266069 A1 | 12/2005 | Simmons et al. |
| 2007/0065502 A1 | 3/2007 | Baksh |
| 2010/0215738 A1* | 8/2010 | Ritter et al. ............... 424/456 |
| 2011/0217275 A1 | 9/2011 | Opheim |
| 2012/0021095 A1* | 1/2012 | Mogna et al. ............... 426/61 |
| 2012/0058095 A1* | 3/2012 | Strozzi et al. ............ 424/93.44 |

FOREIGN PATENT DOCUMENTS

| | | |
|---|---|---|
| AU | 770792 B2 | 3/2004 |
| CA | 2391499 A1 | 5/2001 |
| CA | 2816538 A1 | 7/2012 |
| CN | 102613458 A | 8/2012 |
| EP | 1362588 A1 | 11/2003 |
| EP | 1 514 553 B1 * | 3/2005 |
| IT | RM2009A000104 A1 | 9/2010 |
| JP | 60-218318 A | 11/1985 |
| JP | 2001-178383 A | 7/2001 |
| JP | 2010-90080 A | 4/2010 |
| WO | 2002/066030 A1 | 8/2002 |
| WO | 2004/028460 A2 | 4/2004 |
| WO | 2007/140621 A1 | 12/2007 |
| WO | 2008/046625 A2 | 4/2008 |
| WO | 2010/096564 A2 | 8/2010 |
| WO | 2010103374 A2 | 9/2010 |
| WO | 2011/130487 A1 | 10/2011 |

OTHER PUBLICATIONS

Naidu et al., "Probiotic Spectra of Lactic Acid Bacteria (LAB)," Critical Reviews in Food Science and Nutrition, vol. 38, No. 1, pp. 13-126 (1999).
Favaro-Trindade et al., "Microencapsulation of L. acidophilus (La-05) and B. lactis (Bb-12) and evaluation of their survival at the pH values of the stomach and in bile," J. Microencapsulation, vol. 19, No. 4, pp. 485-494 (2002).
Conway, "Selection criteria for probiotic microorganisms," Asia Pacific J. Clin. Nutr., vol. 5, pp. 10-14 (1996).
Salminen et al., "Clinical uses of probiotics for stabilizing the gut mucosal barrier: successful strains and future challenges," Antonie van Leeuwenhoek, vol. 70, pp. 347-358 (1996).
Shah, "Probiotic Bacteria: Selective Enumeration and Survival in Dairy Foods," J. of Diary Science, vol. 83, No. 4, pp. 894-907 (2000).
Del Piano et al., "Evaluation of the intestinal colonization by microencapsulated probiotic bacteria in comparison to the same uncoated strains," J. of Clinical Gastoenterology, vol. 44, Suppl. 1:S42-46 (2010).
Naidu et al., "Probiotic KE-99 A functional dietary supplement for gastrointestinal health," AgroFOOD industry hi-tech, pp. 18-22 (2004).
Kurtmann et al., "Storage stability of freeze-dried Lactobacillus acidophilus (La-5) in relation to water activity and presence of oxygen and ascorbate," Cryobiology, vol. 58, pp. 175-180 (2009).
International Search Report issued in counterpart application No. PCT/US2011/046901 dated Jun. 1, 2012.
International Preliminary Report on Patentability issued in counterpart application No. PCT/US2011/046901 dated Feb. 12, 2013.
Product brochure regarding Bifa-15 obtained from www.edenfoods.com/mediacenter/brochures.php on Apr. 2, 2014.
Fact sheet regarding Probiotics12Plus obtained from www.nwcnaturals.com/resources on Apr. 2, 2014.
"Improving Probiotic Survival Rates", Food Technol., vol. 55, No. 10, pp. 36-42 (2001).

\* cited by examiner

*Primary Examiner* — Suzanne Ziska

(74) *Attorney, Agent, or Firm* — Fitzpatrick, Cella, Harper & Scinto

(57) ABSTRACT

A softgel capsule containing microencapsulated probiotic bacteria is manufactured such that the softgel capsule is stable for at least about 24 months at room temperature.

20 Claims, No Drawings

PROCESS OF MANUFACTURING A STABLE SOFTGEL CAPSULE CONTAINING MICROENCAPSULATED PROBIOTIC BACTERIA

This application claims the benefit of U.S. Provisional Patent Application No. 61/372,350, filed Aug. 10, 2010, the entire disclosure of which is incorporated by reference herein.

TECHNICAL FIELD

The invention relates to a process of manufacturing a softgel capsule containing microencapsulated probiotic bacteria and to the product made according to this process. More specifically, the product of the invention is stable at room temperature for at least 24 months.

BACKGROUND

Probiotics are microbial-based dietary adjuvants that beneficially affect the host physiology by modulating mucosal and systemic immunity, as well as improving intestinal function and microbial balance in the intestinal tract (Naidu, A. S., et al. (1999), *Probiotic spectra of lactic acid bacteria (LAB)*. Crit. Rev. Food Sci. Nutr. 39:3-126). Various nutritional and therapeutic effects have been ascribed to these probiotics including: modulating immune response, lowering serum cholesterol concentrations, improving lactose intolerance symptoms, increasing resistance to infectious intestinal diseases, decreasing diarrhea duration, reducing blood pressure, and helping to prevent colon cancer.

However, in order to exert these beneficial effects on the host, probiotics must retain their viability and reach the large intestine in large quantities (Favaro-Trindade, C. S., et al. (2002), J Microencapsulation 19(4): 485-494)). Effective probiotic bacteria should be able to survive gastric conditions and colonize the intestine, at least temporarily, by adhering to the intestinal epithelia (Conway, P. (1996), *Selection criteria for probiotic microorganisms*. Asia Pacific J. Clin. Nutr 5:10-14).

Lactic acid bacteria or Lactobacilli are the most commonly used probiotic for incorporation into dairy products such as yogurts, fermented milks and kefirs, and their use is continually becoming more widespread. For example, they are now added in dietary supplement forms, such as powders, capsules and tablets. Bifidobacteria and Streptococci are also commonly used probiotic microorganisms. Lactic acid bacilli generally require an effective delivery system that retains probio-functional activities (i.e., gut adhesion/retention, production of bacteriocins/enzymes) after their revival (Salminen, S., et al. (1996), *Clinical uses of probiotics for stabilizing the gut mucosal barrier: successful strains and future challenges*. Antonie Van Leeuwenhoek 70:347-3581). Furthermore, in addition to increasing in vivo viability and gastrointestinal tract life span, prolonged shelf life at room temperature remains a challenge in the manufacture of effective commercial products. Though freeze-drying of the probiotic bacteria has been shown to be an effective process for preservation and delivery of probiotics, several physico-chemical factors such as humidity, aeration (oxygen availability), processing (i.e., agitation), and temperature could compromise the cell viability and, accordingly, the shelf life.

The stability, viability (i.e., viable microbial content) and quality of products containing probiotic bacteria have been problematic, as evidenced by scientific literature. In one study regarding yogurts, the experiments yielded evidence that 3 of 6 products tested contained no traces of live microorganisms and two contained only low concentrations. Shah (2000) Journal of Dairy Science, 83(4): 894-907. Similar reports have issued with regard to products containing probiotic bacteria distributed in solid dosage forms such as powders, capsules and tablets. The predominant challenges to stability of probiotic bacteria are water activity, physical stress of processing and temperature. It has also been challenging to apply protective measures, such as coatings, that will release the probiotic bacteria at the appropriate delivery site in the body and allow the probiotic to colonize. The appropriate delivery and colonization of the coated probiotic bacteria has recently been confirmed in a newly published study (Del Piano, M., et al. (2010), *Evaluation of the intestinal colonization by microencapsulated probiotic bacteria in comparison to the same uncoated strains*, Journal of Clinical Gastroenterology, 44 Supp. 1: S42-6.)

Oil suspensions have been utilized to increase the viability and shelf life of probiotics. For example, U.S. Patent Application Publication No. 2004/0223956 discloses a composition containing probiotic bacteria suspended in an edible oil and, optionally, encapsulated in a two piece hard shell capsule.

In addition, those in the art have tried using probiotic microspheres to enhance viability and shelf life. For example, U.S. Patent Application Publication No. 2005/0266069 discloses probiotic formulations containing probiotic microspheres having a core of a probiotic bacteria and a cellulosic excipient coated with coating agents and plasticizers.

Experience has long shown that pharmaceuticals or other items for human or animal consumption may be safely and conveniently packaged in a hard or soft gelatin (softgel) shell.

Filled one-piece soft capsules or softgels have been widely known and used for many years and for a variety of purposes and are capable of retaining a liquid fill material. Most frequently, softgels are used to enclose or contain consumable materials such as vitamins, minerals, fruits and botanical extracts and pharmaceuticals in a liquid vehicle or carrier.

Encapsulation within a soft capsule of a solution or dispersion of a nutritional or pharmaceutical agent in a liquid carrier offers many advantages over other dosage forms, such as compressed, coated or uncoated solid tablets, or bulk liquid preparations. Encapsulation of a solution or dispersion permits accurate delivery of a unit dose. Soft capsules provide a dosage form that is easy to swallow and need not be flavored, a good oxygen barrier (i.e., low oxygen permeability through the capsule shell), and tamper protection. Soft capsules are also more easily transported than food products and liquids, such as yogurt and milk.

Probiotics are commercially available in seamless or soft gelatin capsules. Bifa-15™ (Eden Foods, Inc., Clinton, Mich.) is a seamless microencapsulation delivery system for Bifidobacteria, claiming to contain three billion bacteria. The capsules are admixed with oligosaccharides, sweeteners and flavors and presented in individually wrapped, single dose aluminum tubes. The contents are poured into the mouth with the proviso that capsules be swallowed whole and not chewed. Ultra-Dophilus™ (Nature's Plus, Melville, N.Y.) is a conventional-sized soft gelatin capsule containing two billion viable freeze-dried *L. acidophilus*. Probiotocs12Plus™ are soft capsules containing 12 strains of lactic acid bacteria with the aim of a 900 colony forming units potency at the time of manufacture, and no refrigeration required. While each product declares a viability at the time of manufacture, there is no guarantee that the label claim will be met following storage at room temperature, e.g., 22-25° C., in the future. Similar problems in maintaining viability in probiotics contained in gelatin capsules are also evident from patent literature.

The softgels in the art containing probiotic bacteria have been largely unsuccessful. Softgel formulations have not maintained the desired viability, often measured in colony forming units (CFU), for the designed shelf life of the product (typically 2 years), especially at room temperature. The vitality of the probiotic bacteria has tended to decline too rapidly to be successful. This is believed to be due in part to the high water activity Aw (free water) in the softgel environment. This Aw gradient is linked to the softgel production process itself (particularly the encapsulation phase). During this phase, some of the water present in the capsule shell migrates to the formulation within the shell, where it is retained in a free form. In the case of a formulation containing probiotic bacteria, free water activates the probiotic bacteria causing them to perish shortly thereafter.

In addition, the manufacturing process of a softgel challenges the stability of a probiotic bacteria within the softgel as it may stress the probiotic bacteria, even if coated, thereby lessening the viability and stability.

Therefore, there is a need for providing increased viability and stability of probiotic bacteria in products upon prolonged storage at room temperature, as this continues to challenge the industry. In particular, there is a need for a stable softgel capsule containing probiotic bacteria having enhanced viability and shelf life.

SUMMARY OF THE INVENTION

The present invention is directed to a process of manufacturing a softgel capsule containing microencapsulated probiotic bacteria comprising the steps of: (a) providing microencapsulated probiotic bacteria with at least one coating comprising at least one vegetable lipid having a melting point of between 35° C. and 75° C.; (b) suspending the microencapsulated probiotic bacteria in a suspending formulation to make a fill; (c) mixing the fill at low intensity and low temperature to make a mixed fill; (d) reducing agglomerates of the microencapsulated probiotic bacteria in the mixed fill to make a de-agglomerated fill; and (e) encapsulating the de-agglomerated fill in a softgel capsule, wherein the integrity of the coating of the microencapsulated probiotic bacteria is maintained. In a preferred embodiment, the process is conducted while controlling exposure to oxygen, and in a further preferred embodiment, the softgel capsule containing microencapsulated probiotic bacteria is stable for at least about 24 months at room temperature. In a certain embodiment, the agglomerates of the microencapsulated probiotic bacteria are reduced by milling the mixed fill at a temperature below about 33° C. In another preferred embodiment, the microencapsulated probiotic bacteria after encapsulation maintain an average particle diameter size of between about 150 to about 250 microns, and more preferably about 200 microns, and each microencapsulated probiotic bacteria has a particle diameter size of less than about 500 microns.

In a preferred embodiment of the invention, the coating of the microencapsulated probiotic bacteria contains at least one vegetable lipid selected from polyglycerol ester, hydrogenated palm fat, glycerol dipalmitostearate, polyglyceryl-6-distearate, and combinations thereof. In certain preferred embodiments, the suspending formulation comprises at least an oil, a suspending fat or an emulsifier or, at least one oil and at least one material selected from suspending fats, emulsifiers, and combinations thereof.

Mixing in the process of the present invention is preferably performed at a temperature between about 15° C. and about 32° C. and at an intensity less than about 3000 rpm.

The present invention is also directed to a probiotic softgel capsule made according to the process of: (a) providing microencapsulated probiotic bacteria with at least one coating comprising at least one vegetable lipid having a melting point of between about 35° C. and about 75° C.; (b) suspending the microencapsulated probiotic bacteria in a suspending formulation to make a fill; (c) mixing the fill at low intensity and low temperature to make a mixed fill; (d) reducing agglomerates of the microencapsulated probiotic bacteria in the mixed fill to make a de-agglomerated fill; and (e) encapsulating the de-agglomerated fill in a softgel capsule, wherein the integrity of the coating of the microencapsulated probiotic bacteria is maintained.

In certain embodiments, the probiotic softgel capsule is made according to the process conducted while controlling exposure to oxygen and is stable for at least about 24 months at room temperature.

DETAILED DESCRIPTION OF THE INVENTION

The present invention attempts to solve a problem in the art by developing a process of manufacturing a stable softgel capsule containing microencapsulated probiotic bacteria, which enhances the viability of the probiotic bacteria. The inventors discovered the process of the present invention for manufacturing a softgel capsule containing microencapsulated probiotic bacteria, which maintains better stability at room temperature and an average diameter particle size of about 200 microns, each microencapsulated probiotic bacteria having a particle diameter size less than about 500 microns.

The first embodiment is directed to a process of manufacturing a softgel capsule containing microencapsulated probiotic bacteria comprising the steps of: (a) providing microencapsulated probiotic bacteria with at least one coating comprising at least one vegetable lipid having a melting point of between about 35° C. and about 75° C.; (b) suspending the microencapsulated probiotic bacteria in a suspending formulation to make a fill; (c) mixing the fill at low intensity and low temperature to make a mixed fill; (d) reducing agglomerates of the microencapsulated probiotic bacteria in the mixed fill to make a de-agglomerated fill; and (e) encapsulating the de-agglomerated fill in a softgel capsule, wherein the integrity of the coating of the microencapsulated probiotic bacteria is maintained.

The process of the first embodiment of the invention comprises the step of providing microencapsulated probiotic bacteria with at least one coating comprising at least one vegetable lipid having a melting point of between about 35° C. and about 75° C. A purpose of coating the probiotic bacteria is to eliminate contact between the probiotic bacteria and the free water, which migrates from the shell of the softgel capsule to the inner fill formulation. The probiotic bacteria may be coated using any known technique including, but not limited to, a fluid bed technique having a top and/or bottom spray or other coating techniques based on pH induced flocculation. The term microencapsulated, as used herein, means coated with a composition. Generally, microencapsulation is understood to include the coating of particles having an initial size of less than about one micron to around about 200 microns. However, a coating of any reasonable thickness, preferably between about 20 to about 25 microns per layer, is suitable as long as the coating is homogenous and uniform, without any gaps or holes, and forms a suitable barrier layer. For purposes of the invention, providing microencapsulated probiotic bacteria can be accomplished by obtaining microencapsulated probiotic bacteria commercially available or by coating the probiotic bacteria with the described coating.

Any probiotic bacteria may be used in the present invention. Probiotic bacteria can be purchased from commercial sources or cultivated (grown) according to known methods. Probiotics typically belong to the genera *Lactobacillus*, *Bifidobacterium, Streptococcus, Lactococcus, Pediococcus, Propionibacterium, Leuconostoc* and *Saccharomyces*. In the genus *Lactobacillus*, the following species possess probiotic activity: *L. acidophilus, L. crispatus, L. gasseri, L. delbrueckii* group, *L. salivarius, L. casei, L. paracasei, L. plantarum* group, *L. rhamnosus, L. reuteri, L. brevis, L. buchneri, L. fermentum, L. fructivorans, L. ruminis, L. sakei* and *L. vaginalis*. In preferred embodiments of the present invention, the probiotic bacteria are selected from the following species: *L. acidophilus, L. crispatus, L. gasseri, L. delbrueckii* group, *L. salivarius, L. casei, L. paracasei, L. plantarum* group, *L. rhamnosus, L. reuteri, L. brevis, L. buchneri, L. fermentum, B. adolescentis, B. angulatum, B. bifidum, B. breve, B. catenulatum, B. infantis, B. animalis, B lactis, B. longum, B. pseudocatenulatum, S. thermophilus, Sacch. cerevisiae* group and combinations thereof.

In preferred embodiments, the probiotic bacteria used in the present invention is comprised of between one and twelve strains, preferably, from two to six strains, and, more preferably, three strains. The probiotic bacteria may be in any solid form. Preferably, it is in the form of a dehydrated powder manufactured by lyophilization or by spray drying.

The coating comprises at least one vegetable lipid, which has a melting point of between about 35° C. and about 75° C., such that the coating does not melt, soften or degrade in integrity during the process of manufacturing the softgel capsule containing microencapsulated bacteria, during storage of the product, or while transitioning through the gastro-duodenal tract (stomach and duodenum), or in the low pH of the stomach. In theory, the softgel capsule will release the fill containing the microencapsulated probiotic bacteria in the human body in the stomach, and then its contents are delivered to the intestinal tract; the probiotic bacteria will only be activated when delivered to the intestine, which has the appropriate pH to release the probiotic from the coating, and then will colonize for optimal benefit to the host. In a preferred embodiment, the vegetable lipid has a melting point between about 45° C. and about 65° C., more preferably between about 50° C. and about 60° C. In preferred embodiments, the vegetable lipid is polyglyceryl distearate (such as Plurol Stearique WL 1009), glyceryl palmitostearate (such as Precirol Ato 5), saturated fatty acids (such as Revel C), hydrogenated vegetable fats of non-lauric origin and hydrogenated palm fats, stearin and combinations thereof. More preferably, the vegetable lipid is polyglycerol ester, hydrogenated palm fat, glycerol dipalmitostearate or polyglyceryl-6-distearate CAS 61725-93-7, also known as Plurol Stearique WL1009, or a combination thereof.

Optionally, the probiotic bacteria may be coated with more than one layer, i.e., double, triple, etc., each layer being a separate and different coating on the probiotic bacteria, with at least one of the layers being one or a combination of the lipids listed above. In this embodiment, each coating is applied onto the probiotic bacteria in succession. For example, a double coating may be applied to the probiotic bacteria. Multiple coatings may increase the protection of the probiotic bacteria from the free water present in the inside of the softgel capsule. A double coating is further explained in co-pending Italian Patent Application No. RM2009A000104, filed on Mar. 9, 2009, which is incorporated herein by reference.

The process of the first embodiment of the invention comprises the step of suspending the microencapsulated probiotic bacteria in a suspending formulation to make a fill. The suspending formulation of the present invention may be prepared according to any technique known in the art. Without being limited to one theory, it is believed that the suspending formulation effectively limits the contact between the microencapsulated bacteria and the free water ingress from the shell of the softgel capsule to the inner environment, thereby leading to enhanced viability and stability of the probiotic bacteria. The suspending formulation may be adjusted to a suitable thickness to maintain suspension of the powder and to ensure a homogenous mixture. One of ordinary skill in the art would readily understand the thickness required and how to adjust the thickness of the suspension.

In an embodiment of the present invention, the suspending formulation comprises at least an oil, a suspending fat or an emulsifier. In a further embodiment, the suspending formulation comprises at least one oil and at least one material selected from the group consisting of suspending fats, emulsifiers, and combinations thereof. In a preferred embodiment, the suspending formulation is comprised of at least one oil and at least one suspending fat; in another preferred embodiment, the suspending formulation is comprised of at least one oil and at least one emulsifier; in still another preferred embodiment, the suspending formulation comprises at least one each of an oil, a suspending fat and an emulsifier. In certain embodiments, the suspending fat is used as a thickener of the oil and to ensure homogeneity of the suspending formulation.

Oils suitable for use in the present invention include, without limitation, soya bean oil, canola oil, sunflower oil, macadamia oil, peanut oil, grapeseed oil, pumpkin seed oil, linseed oil, flaxseed oil, olive oil, maize oil, safflower oil, sesame oil, pine kernel oil, conjugated linoleic acid, almond oil, peach kernel oil, apricot kernel oil, walnut oil, rapeseed oil, raspberry seed oil, bilberry seed oil, cranberry seed oil, pomegranate seed oil and other fruit seed oils, seabuckthorn oil, chia oil, perilla oil, diaglycerol (DAG) oil, vegetable derived sources of omega 3, fermented sources of eicosapentaenoic acid (EPA), fermented sources of docosahexaenoic acid (DHA), fermented sources of a combination of EPA, DHA and other omega 3s, including fish oil and krill oil, sources of gamma-linolenic acid (GLA) and/or steari-donic acid (SA), fractionated coconut oil, and combinations thereof. Sources of DHA, EPA and ALA include, but are not limited to, fish oils, yeasts or other microorganisms or monocellular sources and vegetable oils, primarily flaxseed, soy, and canola. Sources of GLA include, but are not limited to, evening primrose oil, blackcurrent seed oil, borage oil, and echium oil.

Suspending fats suitable for use in the present invention include, without limitation, monoglycerides of fatty acid, diglycerides of fatty acids, bees wax, glyceryl monostearate, glyceryl mono dioleate, fractionated palm oil derivatives, hydrogenated palm fat, hydrogenated soya oil derivatives, vegetable butters, medium chain triglycerides (MCT), and combinations thereof.

Emulsifiers suitable for use in the present invention include, without limitation, lecithin, polysorbates, sorbitan mono oleates and combinations thereof.

In certain embodiments, the fill preferably contains about 0.5% to about 50% by weight microencapsulated probiotic bacteria and about 50% to about 99.5% by weight of suspending formulation.

The process of the first embodiment of the invention comprises the step of mixing the fill at low intensity and low temperature to make a mixed fill. The mixing is conducted at a low intensity and low temperature so as not to compromise the integrity of, i.e., damage, the coating of the probiotic bacteria and also the cell integrity of the probiotic bacteria. Maintaining the integrity of the coating and particle size of the microencapsulated probiotic bacteria is a key aspect of the enhanced viability and stability of the probiotic bacteria achieved by the present invention.

The integrity of the cell structures of the probiotic bacteria and of the coating of the probiotic bacteria may be analyzed by microscopic analysis to determine whether they remain intact and undamaged. The combination of intact cell structure and coating lead to viable probiotic bacteria that are able to colonize. This ability to colonize may be measured by the total viable count in cfu/g and might be verified through fecal bacterial composition analysis after treatment.

"Low intensity" as used herein refers to mixing at a speed of less than about 3000 rpm (about 50 Hz). Low intensity is also related to selection of blade type, mixer and mixing screen. Preferably, blade type, mixer and mixing screen are selected to minimize shear stress on the suspension, but also to achieve a stable homogenous suspension and reduce agglomeration and particle size without causing damage to the coating on the probiotic bacteria. One of ordinary skill in the art would readily be able to select a suitable blade type, mixer and mixing screen for low intensity and low shear. The intensity of the mixing and the shear may be controlled by a combination of factors readily understood by one skilled in the art. Mixing equipment suitable for use in the present invention includes, without limitation, for example, anchor stirrers or static contra mixing stirrers with or without built in emulsifying/homogenizing equipment, and mixing vessels, including Becomixer, and Skermann mixing vessels, and Ross and Silverson mixers fitted with suitable blades or mixing screens. "Low temperature" as used herein refers to a temperature below about 33° C. The temperature is kept below about 33° C. so that the probiotic bacteria are kept inactive so that the life span is not started until the softgels are swallowed and the temperature of the body activates the probiotic bacteria when delivered to the intended destination. Keeping the temperature low maintains the viability and stability of the probiotic bacteria and the coating. Preferably, the low temperature of the mixing is maintained between about 15° C. and about 32° C., more preferably, between about 20° C. and about 30° C., and most preferably, at about 25° C.

The process of the first embodiment of the invention comprises the step of reducing agglomerates of the microencapsulated probiotic bacteria in the mixed fill to make a de-agglomerated fill. "Reducing agglomerates," in part, means reducing the size of particles and separating particles, which were stuck together. The de-agglomerated fill is preferably de-agglomerated, such that the microencapsulated probiotic bacteria have been predominantly separated from one another. Likewise, this de-agglomerated fill is more preferably a homogenous and uniform fill formulation formed with a controlled particle size, which allows for effective encapsulation and delivery of softgel capsules of good quality. The particles of the microencapsulated probiotic bacteria must be de-agglomerated and reduced to a suitable size for encapsulation. De-agglomeratation can be accomplished by any known means, but must be conducted in such a way as to maintain the integrity of the coating on the probiotic bacteria so that the probiotic bacteria remain protected from the free water that has migrated into the softgel capsule and will deliver viable probiotic bacteria to the intended location in the human body. The de-agglomeration process is preferably conducted in such a way as to maintain the integrity of cell structure of the probiotic bacteria so that they remain viable through the manufacturing process, storage and ingestion and are properly released and activated in the stomach.

In certain embodiments, reducing agglomerates is done by milling. In preferred embodiments, the agglomerate reduction, preferably milling, is conducted at temperatures below 33° C. and, preferably at about 25° C. In addition, this step is preferably conducted in a low humidity environment, which preferably means a humidity below about 20%, and, more preferably, below about 18% humidity. In preferred embodiments, the agglomerate reduction, preferably milling, separates particles which may have agglomerated in the preceding steps, thereby creating a substantially homogenous fill.

In a certain embodiment, milling is accomplished using a three roll milling machine with the gap setting and speed controlled to manage the heat introduced to the fill. Any other equipment, milling or otherwise, known in the art may be used for the agglomerate reduction so long as the temperature, energy, oxygen and water ingress are likewise controlled to manage the heat introduced to the fill. Preferably, ingress of water and oxygen is avoided entirely during milling. In a certain embodiment, reducing agglomerates is a multipart process of milling and deaeration. Deaeration may be performed under vacuum, which extracts air or gas bubbles, and the vacuum will be broken under nitrogen, or any suitable gas, to reduce oxygen exposure. In all of the processing steps disclosed herein, actions may be taken to reduce the aeration and humidity of the fill in order to produce an encapsulated fill with high homogeneity and stability. If air is trapped in the fill, this may cause oxidation problems, reduced stability and encapsulation problems.

Reducing agglomerates refers to standardizing the average particle diameter of the microencapsulated probiotic bacteria and/or de-agglomerating agglomerates of particles formed during the manufacturing process. The average particle diameter size after de-agglomeration may be between about 150 microns to about 250 microns, preferably about 200 microns, with each microencapsulated probiotic bacteria preferably having a particle diameter size of less than about 550 microns, more preferably less than about 500 microns, still more preferably less than about 400 microns and most preferably, with at least about 90% of the particles having a diameter size between about 350 microns and 50 microns.

The process of the first embodiment of the invention comprises the step of encapsulating the de-agglomerated fill in a softgel capsule. Encapsulation of the de-agglomerated fill in a softgel capsule may be performed using any method or manufacturing equipment known in the art. For example, the softgel capsules may be manufactured using a rotary die encapsulation machine. In addition, the softgel capsule may be made from any material known in the art. As a nonlimiting example, the softgel capsule may be made using standard rotary die encapsulation technology and incorporating shell materials for chewable or swallowable purposes chosen from a blend of materials, including, but not limited to gelatin, glycerine, native or modified starches, sources of sorbitol, water, VEGICAPS™ SOFT technology using a selection of carrageenan, modified starch, glycerine and/or sources of sorbitol, water and sodium phosphates.

In a preferred embodiment of the first embodiment of present invention, the process is conducted while controlling exposure to oxygen. This is done to protect the microencapsulated probiotic bacteria from oxidation and increase the stability of the probiotic bacteria. Controlling exposure to oxygen may mean taking steps to not introduce additional oxygen, taking steps to reduce the amount of oxygen present and taking steps to avoid oxygen completely therein. The steps to control exposure to oxygen may be different for each of the process steps of the invention or the same for the steps en masse. Controlling exposure to oxygen is readily understood and may be conducted by any means known by one skilled in the art. In a certain preferred embodiment, each of the process steps is carried out under nitrogen, i.e., a continual nitrogen blanket.

Optionally, the process of the first embodiment of the invention comprises the step of double drying the filled softgel capsule. A double drying process is used to control the drying process so that the softgel capsule is not overly warmed and the probiotic bacteria activated. In a preferred embodiment, the double drying is conducted having a first step of placing the softgel capsules in a tumbler dryer with forced ventilation. In more preferred embodiments, the tumbler dryer is kept at a temperature of about 20° C. and a humidity around about 18% to about 30%, and preferably, about 20%.

In a preferred embodiment, the double drying is conducted having a second step of drying the softgel capsules on trays, rooms or ovens at a temperature of about 18° C. to about 25° C., preferably at about 20° C., and a controlled relative humidity typically between about 8% and about 20%.

Generally, one skilled in the art knows that softgel capsules are dried to the desired hardness and shell water content, specifically suited to the capsule size and density of the fill. The hardness may be determined using a Bareiss Hardness tester, and the shell water content may be determined by measuring humidity using Karl Fisher titration methods.

In the first embodiment of the invention, the integrity of the coating of the microencapsulated probiotic bacteria is maintained. In preferred embodiments, the agglomeration of particles of the microencapsulated probiotic bacteria in the mixed fill is reduced without compromising the integrity of the coating or of the cellular structure of the probiotic bacteria within the coating. It is important to maintain the integrity of the coating in order to keep the probiotic bacteria from contacting the free water within the softgel capsule, which leads to decreased viability. Maintaining the integrity of the coating refers to a coating, which has not been substantially worn away, broken, or thinned at any place thereon such that the probiotic bacteria would come into direct contact with the suspending formulation within the capsule. Compromising the integrity of the coating, by contrast, refers to a coating which has been thinned, worn away, cracked or affected in any way such that the probiotic bacteria would come into direct contact with the suspending formulation within the capsule. Maintaining the integrity of the cellular structure of the probiotic bacteria refers to cellular structure, which has not been deformed or torn. In contrast, compromising the integrity of the cellular structure of the probiotic bacteria within the coating refers to deforming, tearing, scraping, or twisting the cellular structure so that it is weakened. The compromised cellular structure may lead to cells which do not have the capability to colonize in the intestine when delivered.

In a preferred embodiment, the microencapsulated softgel capsule is stable for at least about 24 months at room temperature. Stability of the capsule refers to the maintenance of colony forming units (CFU) of probiotic bacteria within the capsule after a certain period of time. It also may refer to meeting the probiotic activity (cfu/g) denoted on the product label at the end of its shelf life. Stable softgel capsules maintain a total viable cell count of at least about 10% or more of the initial input value per capsule, and more preferably, at least about 20% of the initial input per capsule after about 24 months at room temperature. In another embodiment, stable softgel capsules maintain a total viable cell count between about 10% and about 95% of the initial input value per capsule, and more preferably, between about 20% and about 85% of the initial input per capsule, after about 24 months at room temperature. The initial input value per capsule is preferably between about 1 billion to about 3 billion CFU and, more preferably, about 2 billion CFU.

Herein, "room temperature" preferably refers to a temperature between about 15° C. to about 30° C., more preferably about 20° C. to about 25° C. and a humidity between about 20% and about 75%, and more preferably about 50% to about 60%. Stability at room temperature is important to consumers and generally not provided in the art, as most products must be kept refrigerated in order to maintain the viability of the probiotic bacteria.

In certain preferred embodiments, the packaging of the probiotic softgel capsules provides enhanced protection against water (humidity), oxygen, light and other toxic influences. This packaging supports and protects the stability of the microencapsulated probiotic strains and other ingredients in the fill of the softgel capsules. Preferred packaging includes, but is not limited to, blister packaging with suitable barrier properties, plastic or metal containers with or without a desiccator, and glass jars preferably using an induction seal lid with or without a dessicator. Preferred blister packaging may include triplex blister film of different types, such as standard and high barrier films, including, for example, triplex Flexafarm Sbc (e.g., PVC 250 my+PE 25 my+PVDC 150 g/mq sbc grade) and Aquaba-PVC (e.g., PVC 250 my+AQUABA 160 g/mq), Aclar, Alu-Alu formats, triple layer blister foil (OPA) with soft tempered aluminium in central position, other layers PVC and polyamide, and new generation multilayer blister combined materials. Preferred plastic containers may be made of any suitable plastic materials, for example, HDPE (high density polyethylene), PP (polypropylene), and PET (polyethylene terephthalate), and may also include an integrated or separate dessicant and/or oxygen absorber minipacks or films. Preferred glass bottles may be colored glass, induction sealed, have a plastic or metal lid, and a dessicator or oxygen absorber provision. Preferred metal containers may include aluminum jars, tubes or bottles, which may be induction sealed, have a plastic or metal lid, and/or have a dessicant or oxygen absorber provision.

In the second embodiment of the invention, a probiotic softgel capsule is made according to the process of: (a) providing microencapsulated probiotic bacteria with at least one coating comprising at least one vegetable lipid having a melting point of between about 35° C. and about 75° C.; (b)

suspending the microencapsulated probiotic bacteria in a suspending formulation to make a fill; (c) mixing the fill at low temperature and low pressure to make a mixed fill; (d) reducing agglomerates of the microencapsulated probiotic bacteria in the mixed fill to make a de-agglomerated fill; and (e) encapsulating the de-agglomerated fill in a softgel capsule, wherein the integrity of the coating of the microencapsulated probiotic bacteria is maintained.

The details noted above with regard to the processing steps, i.e., coating, suspending, mixing, reducing agglomerates, etc. are the same for the second embodiment of the disclosure as for the first embodiment of the disclosure. Likewise, the details noted above with regard to controlling exposure to oxygen and the stability of the softgel capsule of the first embodiment are the same as for the second embodiment.

The present invention is not limited to any specific probiotic bacteria or suspending formulation, but to solving the problem of maintained viability and stability of probiotic bacteria in products, and in particular, at room temperature. The following examples will illustrate the process of the present invention in some of the preferred embodiments. Other embodiments within the scope of the claims will be apparent to one skilled in the art.

Example 1

A softgel capsule containing microencapsulated probiotic bacteria was manufactured according to the present invention. *Lactobacillus plantarum* LP01 and *Bifidobacterium breve* BR03 were monocoated with polyglyceryl distearate (Plurol Stearique WL1009) according to the process described in Italian Patent Application No. RM2009A000104. For the suspending formulation, bees wax was melted in soy oil at about 65° C. Soy lecithin was then added to the mixture and the combined formulation cooled at less than or about 25° C. The microencapsulated probiotic bacteria were suspended in the cooled suspending formulation of soy oil, bees wax and soy lecithin and mixed at less than 30° C. for 10 minutes. Table 1 below shows the amount of each component present in the fill. The mixed fill was then milled using a three rolled milling machine maintaining the temperature below 30° C. for 10 minutes and the milled fill passed through a sieve having 600 micron spacing, while under vacuum and under nitrogen to prevent oxidation of the formulation.

The milled fill was then encapsulated in a soft gelatin capsule using a standard rotary die encapsulation machine as follows: the milled fill and the shell material were loaded into separate receivers connected to the machine. The machine prepared from the molten shell material two bands of solid ribbons, which were cooled and lubricated with a mixture of MCT and lecithin. The bands were directed into the position of two rotating dies having specific pockets of the required size and shape for formation of the capsule. The continuing contra-rotation of the opposed dies then formed a seal between the two ribbons contacting the dies while the fill material was simultaneously injected into the body of the capsule so formed. Lastly, the continuing rotation of the dies cuts the newly formed capsule from the ribbon.

The softgel capsules were subsequently divided into two batches, and each batch was dried in two steps. First, one batch of the softgel capsules was dried by a standard process, i.e., placed in a tumbler drier with forced ventilation, with the air taken from the external environment, at approximately 20% R.H. and 20° C. for 80 minutes. The second batch of the softgel capsules was dried by a slower process, i.e., placed in a tumbler drier with forced ventilation, with the air taken from the external environment, at approximately 20% R.H. and 20° C. for 122.5 minutes. In the second step, the softgel capsules from each batch were placed on trays and stacked in drying cabinets having special ventilation with dry and conditioned air at approximately 20% R.H. and 20° C. The softgel capsules were dried to a stabilized hardness of 10 N measured using the Bareiss Hardness tester.

Each batch of prepared softgel capsules was split into three groups with one group stored in dark glass bottles with aluminium caps, the second group stored in blister triplex pockets, and the third group stored in "bulk," meaning that the softgel capsules were stored in impermeable, triple layer cellophane sachets. The three groups of softgel capsules were stored at 25° C. and parameters assessed, which reliably predict subsequent stability of strains through shelf-life, after 6 months and after 18 months of storage. The integrity of the cell structure of the probiotic bacteria and of the coating were analyzed by microscopic analysis. If the cell structure and coating of the probiotic bacteria remain intact, viable probiotic bacteria are able to colonize. This ability is measured by total viable count in cfu/g and might be verified by fecal bacterial composition analysis after treatment. The softgel capsule containing microencapsulated probiotic bacteria was manufactured to provide the target of 2 billion CFU per capsule (as sum of the two strains) at 24 months of shelf life at room temperature. Table 3 below shows the batches of softgel capsules that were prepared and Tables 4 and 5 show the results of the stability assessment.

TABLE 1

| Ingredient | Quantity/capsule (mg/capsule) |
|---|---|
| *Lactobacillus plantarum* LP01 (LMG P-21021) (monocoated) | $5 \times 10^{11}$ CFU/cps* |
| *Bifidobacterium breve* BR03 (DSM 16604) (monocoated) | $5 \times 10^{11}$ CFU/cps* |
| Soy Oil | 390.0** |
| Soy Lecithin | 2.0 |
| Bees wax | 58.0** |

*This quantity was the measured potency of the specific batch.
**This quantity provided suitable thickness of the suspension for encapsulation.

Example 2

A milled fill for containing microencapsulated probiotic bacteria was manufactured according to the present invention. *Lactobacillus plantarum* LP01 and *Bifidobacterium breve* BR03 were monocoated with polyglyceryl distearate (Plurol Stearique WL1009) according to the process described in Italian Patent Application No. RM2009A000104. For the suspending formulation, soy oil was heated to about 65° C. Soy lecithin and glyceryl monostearate were then added to the mixture and the combined formulation cooled at less than or about 25° C. The microencapsulated probiotic bacteria were suspended in the cooled suspending formulation of soy oil, glyceryl monostearate and soy lecithin and mixed at less than 30° C. for 10 minutes. Table 2 below shows the amount of each component present in the fill. The mixed fill was then milled using a three rolled milling machine at less than 30° C. for 10 minutes and the milled fill passed through a sieve having 600 micron spacing, while under vacuum and under nitrogen.

Initial stability of the microencapsulated probiotic bacteria within the milled fill was tested by microscopic analysis to verify the integrity of the coating and cell structure of the probiotic bacteria. The number of coated probiotic bacteria was calculated as the difference between the total number of probiotic bacteria and the uncoated probiotic bacteria. These test results showed similar initial stability as the initial stability results for the milled fill of Example 1, e.g., no significant damage to the cellular structure of the probiotic bacteria or coating. Therefore, it was assumed that the encapsulated milled fill of Example 2 would have similar results to Example 1. Therefore, Example 2 was not encapsulated or the stability of a softgel containing such a fill studied further.

TABLE 2

| Ingredient | Quantity/capsule (mg/capsule) |
|---|---|
| *Lactobacillus plantarum* LP01 (LMG P-21021) (monocoated) | $5 \times 10^{11}$ CFU/cps* |
| *Bifidobacterium breve* BR03 (DSM 16604) (monocoated) | $5 \times 10^{11}$ CFU/cps* |
| Soy Oil | 429.0** |
| Soy Lecithin | 2.0 |
| Glyceryl monostearate (GMS) | 27.2** |

*This quantity was the measured potency of the specific batch.
**This quantity provided suitable thickness of the suspension for encapsulation.

Comparative Example 1

A softgel capsule containing microencapsulated probiotic bacteria was manufactured according to the process of Example 1, except that the mixed fill was encapsulated without undergoing the milling (agglomerate reduction) step. Without milling, the softgel capsules produced are of lower quality and have increased leakage. Additional processing steps may be added to reduce leakage in other ways, but these steps would increase costs to a potentially commercially unacceptable amount.

The softgel capsules were subsequently divided into two batches, and each part was dried in two steps. First, one batch of the softgel capsules was dried by a standard process, i.e., placed in a tumbler drier with forced ventilation, with the air taken from the external environment, at approximately 20% R.H. and 20° C. for 48 minutes. The second batch of the softgel capsules was dried by a slower process, i.e., placed in a tumbler drier with forced ventilation, with the air taken from the external environment, at approximately 20% R.H. and 20° C. for 122.5 minutes. In the second step, the softgel capsules from each batch were placed on trays and stacked in drying cabinets having special ventilation with dry and conditioned air. The softgel capsules were dried to a stabilized hardness of 9 N measured using the Bareiss Hardness tester.

Each batch of prepared softgel capsules was split into three groups with one group stored in dark glass bottles with aluminium caps, the second group stored in blister triplex pockets, and the third group stored in "bulk." The three groups of softgel capsules were stored at 25° C. and parameters assessed, which reliably predict subsequent stability of strains through shelf-life, after 6 months and 18 months of storage. The integrity of the cell structure of the probiotic bacteria and of the coating was tested by microscopic analysis. The number of coated probiotic bacteria was calculated as the difference between the total number of probiotic bacteria and the uncoated probiotic bacteria. If the cell structure and coating of the probiotic bacteria remain intact, viable probiotic bacteria are able to colonize.

The softgel capsule containing microencapsulated probiotic bacteria was manufactured to provide the target of 2 billion CFU per capsule (as sum of the two strains) at 24 months of shelf life at room temperature. Table 3 below shows the batches of softgel capsules that were prepared, and Tables 4 and 5 shows the results of the stability assessment after 6 and 18 months, respectively.

TABLE 3

| CODE | Fill preparation process | Primary drying | Secondary drying | Packaging |
|---|---|---|---|---|
| EXAMPLE 1 | With milling | Standard dryer | Drying Cabinets | Bulk |
|  |  | Standard dryer |  | Dark glass bottle |
|  |  | Standard dryer |  | Triplex blister |
|  |  | Slow dryer |  | Bulk |
|  |  | Slow dryer |  | Dark glass bottle |
|  |  | Slow dryer |  | Triplex blister |
| EXAMPLE 2 | Only bench trial | Not performed | Not performed | Not performed |
| COMPARATIVE EXAMPLE 1 | No milling | Standard dryer | Drying Cabinets | Bulk |
|  |  | Standard dryer |  | Dark glass bottle |
|  |  | Standard dryer |  | Triplex blister |
|  |  | Slow dryer |  | Bulk |
|  |  | Slow dryer |  | Dark glass bottle |
|  |  | Slow dryer |  | Triplex blister |

TABLE 4

| | | T zero | Long-term stability at 25° C. 6 months* | | | |
|---|---|---|---|---|---|---|
| Packaging code | Process | viable cell count ($10^9$ CFU/g) | Total cells ($10^9$ CFU/g) | Coated cells ($10^9$ CFU/g) | % of coated cells | Half-life (days) |
| Example 1 (bulk) | With milling/ standard dryer | 20.3 | 13.8 | 13.05 | 94.6 | 375 |
| Example 1 (bottle) |  | 19.2 | 13.2 | 12.9 | 97.7 | 387 |
| Example 1 (blister) |  | 20.1 | 14.7 | 14.5 | 98.6 | 463 |
| Example 1 (bulk) | With milling/ slow dryer | 18.9 | 13.3 | 13.05 | 98.1 | 412 |
| Example 1 (bottle) |  | 20.6 | 14.8 | 14.36 | 97.0 | 438 |
| Example 1 (blister) |  | 19.5 | 14.2 | 13.6 | 95.8 | 457 |
| Comp. Ex. 1 (bulk) | Without milling/ standard dryer | 19.8 | 13.4 | 12.97 | 96.8 | 371 |
| Comp. Ex. 1 (bottle) |  | 19.3 | 13 | 12.45 | 95.8 | 367 |
| Comp. Ex. 1 (blister) |  | 21.1 | 14.8 | 14.5 | 98.0 | 408 |
| Comp. Ex. 1 (bulk) | Without milling/ slow dryer | 20.3 | 12.8 | 12.15 | 94.9 | 314 |
| Comp. Ex. 1 (bottle) |  | 19.1 | 13.3 | 12.3 | 92.5 | 400 |
| Comp. Ex. 1 (blister) |  | 20 | 13.7 | 12.9 | 94.2 | 383 |

*Actual duration of storage was 209 days.

TABLE 5

| Packaging code | Process | T zero viable cell count ($10^9$ CFU/g) | Long-term stability at 25° C. 18 months* | | | |
|---|---|---|---|---|---|---|
| | | | Total cells ($10^9$ CFU/g) | Coated cells ($10^9$ CFU/g) | % of coated cells | Half-life (days) |
| Example 1 (bulk) | With milling/ standard dryer | 20.3 | 7 | 6.7 | 95.7 | 365 |
| Example 1 (bottle) | | 19.2 | 6.7 | 6.4 | 95.5 | 369 |
| Example 1 (blister) | | 20.1 | 6.6 | 5.9 | 89.4 | 349 |
| Example 1 (bulk) | With milling/ slow dryer | 18.9 | 6.0 | 5.5 | 91.7 | 338 |
| Example 1 (bottle) | | 20.6 | 6.8 | 6.4 | 94.1 | 350 |
| Example 1 (blister) | | 19.5 | 6.2 | 5.5 | 88.7 | 339 |
| Comp. Ex. 1 (bulk) | Without milling/ standard dryer | 19.8 | 6.1 | 5.5 | 90.2 | 330 |
| Comp. Ex. 1 (bottle) | | 19.3 | 5.8 | 5.2 | 89.7 | 323 |
| Comp. Ex. 1 (blister) | | 21.1 | 5.6 | 5.3 | 94.6 | 293 |
| Comp. Ex. 1 (bulk) | Without milling/ slow dryer | 20.3 | 5.8 | 5.3 | 91.4 | 310 |
| Comp. Ex. 1 (bottle) | | 19.1 | 6.3 | 6.0 | 95.2 | 350 |
| Comp. Ex. 1 (blister) | | 20 | 5.5 | 5.2 | 94.5 | 301 |

*Actual duration of storage was 560 days.

The stability data after 6 months shown in Table 4 and after 18 months in Table 5 illustrate that stability of probiotic bacteria in softgels after milling is generally higher than probiotic bacteria in samples that were not milled, and milling has a greater influence on stability than the type of drying. Each of the selected packaging types provided suitable protection against oxidation and other potential detrimental effects on stability. Table 4 also shows that a high percentage of coated cells (>90%) remain at 6 months. Likewise, Table 5 shows that a high percentage of coated cells (>88%) remain in each packaging type tested at 18 months. This suggests that viable cells present even after 18 months were very robust.

Further, the results above show that milling according to the present invention does not cause more damage to the coating on the probiotic bacteria than preparing the process without milling (Comparative Example 1). Since milling is an important step in the process of manufacturing a softgel capsule that is commercially acceptable, e.g., to maintain reasonable costs, to reduce leakage, etc., milling without damaging the coating on the probiotic bacteria is an important benefit of the present invention.

Example 3

A softgel capsule containing microencapsulated probiotic bacteria was manufactured according to the process of Example 1, but on a full batch scale up. The softgel capsules were mixed using full scale mixing equipment. The fill material was deaerated under vacuum and the vacuum was broken under nitrogen. This process facilitates avoidance of trapped gas (mainly oxygen) in the final product, which in turn amounts to reduced oxidation of any potential remaining oxygen after encapsulation. In addition, this process helps to ensure dose content uniformity between capsules. This fill material was then encapsulated and dried using a standard process, i.e., placing the softgel capsules in a tumbler drier with forced ventilation, with the air taken from the external environment, at approximately 20% R.H. and 20° C. for 135 minutes. In the second drying step, the softgel capsules from each batch were placed on trays and stacked in drying cabinets having special ventilation with dry and conditioned air. The softgel capsules were dried to a stabilized hardness of 9 N measured using the Bareiss Hardness tester and less than 20% ERH (Equilibrium Relative Humidity).

The dried softgel capsules were split into three groups with one group stored in dark glass bottles with aluminium caps, the second group stored in blister triplex pockets, and the third group stored in plastic Duma containers. The three groups of softgel capsules were stored at 25° C. for 3 months and parameters assessed to evaluate their robustness. The integrity of the cell structure of the probiotic bacteria and of the coating were tested by microscopic analysis. The number of coated probiotic bacteria was calculated as the difference between the total number of probiotic bacteria and the uncoated probiotic bacteria. If the cell structure and coating of the probiotic bacteria remain intact, viable probiotic bacteria are able to colonize. The softgel capsule containing microencapsulated probiotic bacteria was manufactured to provide the target of 2 billion CFU per capsule (as sum of the two strains) at 24 months of shelf life at room temperature.

Table 6 shows the processing, drying and packaging of Example 3. To test the robustness of the batch of Example 3, samples were taken throughout the manufacturing process of the full scale batch and also after 1 month and 3 months of storage to show the increased stability obtained through careful processing (Table 7) and through selective packaging (Table 8). The temperature and mixing speeds were carefully controlled and monitored.

TABLE 6

| Batch code | Process | Type of primary drying | Type of secondary dryer | Packaging |
|---|---|---|---|---|
| Example 3 Full Scale Batch | Milling & Deaeration | Slow dryer | Drying Cabinets | Dark glass bottle with aluminum cap Plastic bottle Triplex Blister |

TABLE 7

| In Process Samples: Full scale batch manufacture | Mixing speed specification | Measured mixing speed | Mix temperature | Theoretical total viable cell count ($10^9$ CFU/g) | Actual total viable cell count ($10^9$ CFU/g) |
|---|---|---|---|---|---|
| Suspension after 10 minutes mixing | Less than 3000 rpm (50 hz) | 25.6 Hz | 23° C. | 20 | 18.7 |

TABLE 7-continued

| In Process Samples: Full scale batch manufacture | Mixing speed specification | Measured mixing speed | Mix temperature | Theoretical total viable cell count ($10^9$ CFU/g) | Actual total viable cell count ($10^9$ CFU/g) |
|---|---|---|---|---|---|
| Suspension after 17 minutes of mixing | Less than 3000 rpm (50 hz) | 32.2 Hz | 25° C. | 20 | 19.3 |
| Suspension after sieving & deaeration Top of vessel | N/A | N/A | 25° C. | 20 | 19 |
| Suspension after sieving & deaeration Bottom of vessel. | N/A | N/A | 25° C. | 20 | 22 |
| Capsules after primary drying | N/A | N/A | N/A | 20 | 21 |
| Capsules after secondary drying | N/A | N/A | N/A | 20 | 21 |

TABLE 8

| | | Long-term stability at 25° C. | |
|---|---|---|---|
| | | 1 month | 3 months** |
| Sample identification | T zero viable cell count ($10^9$ CFU/g) | Days of storage | Viable cell count ($10^9$ CFU/g) | Viable cell count ($10^9$ CFU/g) |
| Ex. 3 (blister) | | | | |
| Total cells | 21 | 32 | 19.3 | 16.5 |
| Total coated cells | 17.1 | 31 | 16.5 | 14 |
| % Coated | 81.4 | — | 85.5 | 84.8 |
| Ex. 3 (glass bottle) | | | | |
| Total cells | 18.7 | 32 | 17.4 | 15.1 |
| Total coated cells | 15 | 31 | 14.7 | 13.5 |
| % Coated | 80.2 | — | 84.5 | 89.4 |
| Ex. 3 (plastic bottle) | | | | |
| Total cells | 19 | 32 | 17.8 | 15.6 |
| Total coated cells | 16.1 | 31 | 15.4 | 13.6 |
| % Coated | 84.7 | — | 86.5 | 87.2 |

**Actual duration of storage was 87 days.

Table 8 illustrates that after 1 month, and after 3 months of storage after full batch scale up, over 80% of coated cells remain. In comparing the percent of coated cells remaining after storage of Example 1, shown in Tables 4 and 5, with the percent of coated cells remaining after storage of Example 3, some reduction in percentage is always assumed when the process is scaled up. The results achieved here were positive since over 80% still remained after 3 months of storage (Table 8). Accordingly, the full batch scale up did not significantly negatively affect the viability of the probiotic bacteria.

Example 4

A softgel capsule containing microencapsulated probiotic bacteria was manufactured according to the process of Example 3, except that the three groups with one group stored in dark glass bottles with aluminium caps, the second group stored in blister triplex pockets, and the third group stored in plastic Duma containers, were each split into three subgroups with one subgroup stored at 25° C. for 3 months, the second subgroup stored at 30° C. for 3 months, and the third subgroup stored at 33° C. for 3 months.

TABLE 9

| | T zero viable cell count ($10^9$ CFU/g) | 3 months** stability data | | |
|---|---|---|---|---|
| Sample identification | | 25° C. | 30° C. | 33° C. |
| Ex. 4 (blister) | | | | |
| Total cells | 21 | 16.5 | 15.0 | 3.4 |
| Total coated cells* | 17.1 | 14.0 | 12.9 | 2.7 |
| % Coated | 81.4 | 84.8 | 86.0 | 79.4 |
| Ex. 4 (glass bottle) | | | | |
| Total cells | 18.7 | 15.1 | 13.0 | 4.1 |
| Total coated cells* | 15 | 13.5 | 11.5 | 3.8 |
| % Coated | 80.2 | 89.4 | 88.5 | 92.7 |
| Ex. 4 (plastic bottle) | | | | |
| Total cells | 19 | 15.6 | 14.0 | 3.1 |
| Total coated cells* | 16.1 | 13.6 | 12.4 | 2.8 |
| % Coated | 84.7 | 87.2 | 88.6 | 90.3 |

**Actual duration of storage was 87 days.

TABLE 10

| Sample identification | Days of storage | T zero viable cell count ($10^9$ CFU/g) | 1 month stability data | | | |
|---|---|---|---|---|---|---|
| | | | 25° C. | 30° C. | 33° C. | 37° C. |
| Ex. 4 (blister) | | | | | | |
| Total cells | 32 | 21 | 19.3 | 18.2 | 13.9 | 8.4 |
| Total coated cells* | 31 | 17.1 | 16.5 | 15.7 | 12.6 | 8.1 |
| % Coated | — | 81.4 | 85.5 | 86.3 | 90.6 | 96.4 |
| Ex. 4 (glass bottle) | | | | | | |
| Total cells | 32 | 18.7 | 17.4 | 17 | 12.8 | 6.8 |
| Total coated cells* | 31 | 15 | 14.7 | 14.2 | 11.3 | 6.3 |
| % Coated | — | 80.2 | 84.5 | 83.5 | 88.3 | 92.6 |
| Ex. 4 (plastic bottle) | | | | | | |
| Total cells | 32 | 19 | 17.8 | 17.3 | 13.4 | 6.3 |
| Total coated cells* | 31 | 16.1 | 15.4 | 15 | 12 | 5.9 |
| % Coated | — | 84.7 | 86.5 | 86.7 | 89.6 | 93.7 |

Tables 9 and 10 show that temperature during storage affects the viability of the probiotic strains, e.g., temperatures of 33° C. and above have a clear impact on viability of the probiotic strains, even though the coating efficiency (%) was not effected. Accordingly, temperature and energy parameters during storage need to be carefully controlled. It may be understood then that the temperature during other processing steps, e.g., milling, also affects the viability of the strains and should be carefully controlled to remain below 33° C. For example, Table 7 shows that during the full batch scale up, the temperature of the fill did not exceed 25° C., and this controlled paramenter contributed to the longer term stability of the probiotic strains.

Based on the collected data, the results of the full batch scale up (Example 3) confirm the superior robustness of the softgel capsule manufacturing process of the present disclosure. In conclusion, the stability of the probiotic strains is clearly related to the integrity of the coating as demonstrated by the study of the influence of temperature on the stability of the strains (Example 4). At elevated temperatures, the uncoated cells degrade and, after 1 month at 37° C., the remaining alive strains are almost all coated (>90%). The coating is designed to deliver the probiotic strain in the intestine and to allow it to colonize in the gut at body temperature. Increased temperature and humidity may prematurely activate the probiotic strain before it reaches the intended colonization site, which can result in failure to colonize at the target site and, in turn, failure to deliver the intended benefit to the body.

In conclusion, from an overall analysis of the data collected, it appears that a satisfactory amount of the probiotic bacteria processed according to the present disclosure will remain viable throughout the shelf life. It could be assumed from this data that a total viable cell count of at least 2 billion CFU/capsule would remain at expiration time (1 billion of each strain). A concentration of microencapsulated probiotic bacteria five times lower than the amount of uncoated bacteria is able to colonize the human intestine with the same effectiveness. In addition, when the microencapsulated probiotic bacteria are delivered to the intended colonization site in the intestine, they are 5 times more likely to colonize than uncoated probiotic bacteria. See Del Piano, M., et al. (2010), *Evaluation of the intestinal colonization by microencapsulated probiotic bacteria in comparison to the same uncoated strains*, Journal of Clinical Gastroenterology, 44 Supp. 1: S42-6.

Thus, there are numerous advantages to the process of the present invention. The resulting softgel capsule containing microencapsulated probiotic bacteria has the unexpected stability, e.g., CFU, and number of coated probiotic bacteria for better delivery of probiotic bacteria to the human digestive system.

Numerous alterations, modifications, and variations of the preferred embodiments disclosed herein will be apparent to those skilled in the art, and they are all anticipated and contemplated to be within the spirit and scope of the claimed invention. For example, although specific embodiments have been described in detail, those with skill in the art will understand that the preceding embodiments and variations can be modified to incorporate various types of substitute, additional or alternative materials. Accordingly, even though only few variations of the present invention are described herein, it is to be understood that the practice of such additional modifications and variations and the equivalents thereof, are within the spirit and scope of the invention as defined in the following claims. All patent applications, patents, and other publications cited herein are incorporated by reference in their entirety.

What is claimed is:

1. A process of manufacturing a softgel capsule containing microencapsulated probiotic bacteria comprising the steps of:
   (a) providing microencapsulated probiotic bacteria with at least one coating comprising at least one vegetable lipid having a melting point of between about 35° C. and about 75° C.;
   (b) suspending the microencapsulated probiotic bacteria in a suspending formulation to make a fill;
   (c) mixing the fill at an intensity less than 3000 rpm and a temperature below 33° C. to make a mixed fill;
   (d) reducing agglomerates of the microencapsulated probiotic bacteria in the mixed fill to make a de-agglomerated fill; and
   (e) encapsulating the de-agglomerated fill in a softgel capsule,
   wherein the integrity of the coating of the microencapsulated probiotic bacteria is maintained.

2. The process according to claim 1, wherein the process is conducted while controlling exposure to oxygen.

3. The process according to claim 2, wherein the softgel capsule containing microencapsulated probiotic bacteria is stable for at least about 18 months at room temperature.

4. The process according to claim 1, wherein the agglomerates of the microencapsulated probiotic bacteria are reduced by milling the mixed fill at a temperature below about 33° C.

5. The process according to claim 1, wherein the microencapsulated probiotic bacteria after encapsulation maintain an average particle diameter size of between about 150 to about 250 microns and less than about 550 microns.

6. The process according to claim 5, wherein the microencapsulated probiotic bacteria after encapsulation maintain an average particle diameter size of about 200 microns and each microencapsulated probiotic bacteria has a particle diameter size less than about 500 microns.

7. The process according to claim 1, wherein the at least one vegetable lipid is selected from the group consisting of polyglycerol ester, hydrogenated palm fat, glycerol dipalmitostearate, polyglyceryl-6-distearate, and combinations thereof.

8. The process according to claim 1, wherein the suspending formulation comprises at least an oil, a suspending fat or an emulsifier.

9. The process according to claim 8, wherein the suspending formulation comprises at least one oil and at least one material selected from the group consisting of suspending fats, emulsifiers, and combinations thereof.

10. The process according to claim 8, wherein the at least one oil is selected from the group consisting of soya bean oil, canola oil, sunflower oil, macadamia oil, peanut oil, grapeseed oil, pumpkin seed oil, linseed oil, flaxseed oil, olive oil, maize oil, safflower oil, sesame oil, pine kernel oil, conjugated linoleic acid, almond oil, peach kernel oil, apricot kernel oil, walnut oil, rapeseed oil, raspberry seed oil, bilberry seed oil, cranberry seed oil, pomegranate seed oil and other fruit seed oils, seabuckthorn oil, chia oil, perilla oil, diaglycerol oil, vegetable derived sources of omega 3, fermented sources of eicosapentaenoic acid, fermented sources of docosahexaenoic acid, fermented sources of a combination of eicosapentaenoic acid, docosahexaenoic acid and other omega 3s, sources of gamma-linolenic acid and/or stearidonic acid, fractionated coconut oil, and combinations thereof.

11. The process according to claim 8, wherein suspending fats are selected from the group consisting of monoglycerides of fatty acids, diglycerides of fatty acids, bees wax, glyceryl monostearate, glyceryl mono dioleate, fractionated palm oil derivatives, hydrogenated palm fat, hydrogenated soya oil derivatives, vegetable butters, medium chain triglycerides, and combinations thereof.

12. The process according to claim 8, wherein emulsifiers are selected from the group consisting of lecithin, polysorbates, sorbitan mono oleates, and combinations thereof.

13. The process according to claim 1, wherein the mixing is conducted at a temperature between about 15° C. and about 32° C.

14. The process according to claim 1, wherein the reducing of agglomerates is performed with the de-agglomerated fill maintaining a temperature below about 33° C. and in a low humidity environment.

15. The process according to claim 1, further comprising the step of:
(f) double drying the filled softgel capsule.

16. The process according to claim 15, wherein the double drying is comprised of drying the capsules in a tumbler drier at forced ventilation, followed by drying the capsule on trays stacked inside drying cabinets, wherein the temperature is from about 18° C. to about 25° C. and the relative humidity is at about 8% to about 20%.

17. A probiotic softgel capsule made according to the process of claim 1.

18. The probiotic softgel capsule according to claim 17, wherein the process is conducted while controlling exposure to oxygen.

19. The probiotic softgel capsule according to claim 18, wherein the softgel capsule is stable for at least about 24 months at room temperature.

20. A process of manufacturing a softgel capsule containing microencapsulated probiotic bacteria comprising the steps of:
(a) providing microencapsulated probiotic bacteria with at least one coating comprising at least one vegetable lipid having a melting point of between about 35° C. and about 75° C.;
(b) suspending the microencapsulated probiotic bacteria in a suspending formulation to make a fill;
(c) mixing the fill at an intensity less than 3000 rpm and a temperature below 33° C. to make a mixed fill;
(d) reducing agglomerates of the microencapsulated probiotic bacteria in the mixed fill to make a de-agglomerated fill; and
(e) encapsulating the de-agglomerated fill in a softgel capsule,
wherein the integrity of the coating of the microencapsulated probiotic bacteria is maintained, and
wherein the softgel capsule is stable for at least about 18 months at room temperature.

* * * * *